United States Patent
Rego et al.

(10) Patent No.: US 12,121,376 B2
(45) Date of Patent: Oct. 22, 2024

(54) SYSTEMS AND METHODS FOR APPLYING FORCE TO BREASTS FOR IMAGING

(71) Applicant: Hologic, Inc., Marlborough, MA (US)

(72) Inventors: Alan Rego, Woodbury, CT (US);
Andrew Smith, Lexington, MA (US);
David Wolff, Hockessin, DE (US);
Kenneth F. Defreitas, Patterson, NY (US)

(73) Assignee: Hologic, Inc., Marlborough, MA (US)

( * ) Notice: Subject to any disclaimer, the term of this patent is extended or adjusted under 35 U.S.C. 154(b) by 261 days.

(21) Appl. No.: 17/574,777

(22) Filed: Jan. 13, 2022

(65) Prior Publication Data
US 2022/0218294 A1 Jul. 14, 2022

Related U.S. Application Data

(60) Provisional application No. 63/136,832, filed on Jan. 13, 2021.

(51) Int. Cl.
*A61B 6/04* (2006.01)
*A61B 6/50* (2024.01)

(52) U.S. Cl.
CPC .......... *A61B 6/0414* (2013.01); *A61B 6/0435* (2013.01); *A61B 6/502* (2013.01)

(58) Field of Classification Search
CPC ..... A61B 6/0414; A61B 6/0435; A61B 6/502; A61B 6/46; A61B 6/5217; A61B 6/54
See application file for complete search history.

(56) References Cited

U.S. PATENT DOCUMENTS

| | | | |
|---|---|---|---|
| 2007/0121782 A1 | 5/2007 | Sendai | |
| 2014/0328458 A1* | 11/2014 | Erhard | A61B 6/0414 702/19 |
| 2019/0287241 A1* | 9/2019 | Hill | A61B 6/5282 |

FOREIGN PATENT DOCUMENTS

| | | | | |
|---|---|---|---|---|
| CN | 101373479 A | * | 2/2009 | |
| EP | 3263035 | | 1/2018 | |
| EP | 3263035 A1 | * | 1/2018 | A61B 6/04 |
| WO | 2019/226792 | | 11/2019 | |

OTHER PUBLICATIONS

Translation of CN-101373479-A (Year: 2009).*
PCT International Search Report and Written Opinion in International Application PCT/US2022/012372, mailed Apr. 4, 2022, 14 pages.
PCT International Preliminary Report on Patentability in International Application PCT/US2022/012372, mailed Jul. 27, 2023, 8 pages.

* cited by examiner

*Primary Examiner* — David P Porta
*Assistant Examiner* — Mamadou Faye
(74) *Attorney, Agent, or Firm* — Merchant & Gould P.C.

(57) ABSTRACT

A method of compressing a breast of a patient with a breast imaging system includes obtaining an x-ray area of the breast of the patient. The x-ray area of the breast is compared to a data set, and a target force is based at least in part on the comparison is identified. A compressive force is applied to the breast, and is based at least in part on the target force. The breast is imaged with the breast imaging system.

25 Claims, 11 Drawing Sheets

SYSTEMS AND METHODS FOR APPLYING FORCE TO BREASTS FOR IMAGING

CROSS-REFERENCE TO RELATED APPLICATIONS

This application claims the benefit of priority to U.S. Provisional Application No. 63/136,832, filed Jan. 13, 2021, which application is hereby incorporated in its entirety by reference.

BACKGROUND

Compression during breast imaging, such as mammography and tomosynthesis imaging, serves a number of purposes. For example, it may: (1) make the breast thinner in the direction of x-ray flux and thereby reduces patient radiation exposure from the level required to image the thicker parts of a breast that are not compressed; (2) make the breast more uniform in thickness in the direction of x-ray flux and thereby facilitates more uniform exposure at the image plane over the entire breast image; (3) immobilize the breast during the x-ray exposure and thereby reduces image blurring; and (4) bring breast tissues out from the chest wall into the imaging exposure field and thus allows for more tissue imaging. As the breast is being compressed, typically a technician manipulates the breast to position it appropriately and counter the tendency that compression has of pushing breast tissue toward the chest wall and out of the image field.

Standard compression methods for breast imaging use a movable, rigid, radiolucent compression paddle. The breast is placed on a breast support platform that typically is flat, and the paddle then compresses the breast, usually while a technician or other health professional is holding the breast in place. The technician may also manipulate the breast to ensure proper tissue coverage in the image receptor's field of view.

One known challenge in mammography and breast tomosynthesis is the discomfort the patient may feel when the breast is compressed, which must be done with sufficient force to immobilize the breast and spread out the breast tissues for x-ray imaging. Discomfort may potentially cause the patient to move, which negatively impacts image quality. Discomfort may also potentially dissuade patients from getting screened for breast cancer. Another known challenge is to ensure that the imaged field includes the desired amount of breast tissue.

SUMMARY

The technologies described herein include systems for compressing a breast, as well as particular methods for performing compression of a breast. The methods described herein may be performed by systems having various configurations. Several examples of such systems are described.

In one aspect, the technology relates to a method of compressing a breast of a patient with a breast imaging system, including: obtaining an x-ray area of the breast of the patient, wherein the x-ray area is obtained from a prior x-ray image of the breast of the patient; comparing the x-ray area of the breast to a data set, wherein the data set relates the x-ray area of the breast to the target force; based at least in part on the comparison, identifying a target force; applying a compressive force to the breast, wherein the compressive force is based at least in part on the target force; and imaging the breast with the breast imaging system. In an example, wherein when the prior x-ray image of the breast is unavailable, obtaining the x-ray area includes: receiving a distance measurement of a distance of a nipple of the breast from a chest wall of the patient; and estimating the x-ray area based at least in part on the received distance measurement. In another example, estimating the x-ray area includes comparing the distance measurement to a reference distance obtained from a reference. In still another example, the target force is obtained from a look-up table.

In another example of the above aspect, the target force is obtained by applying the x-ray area to an algorithm. In an example, the method further includes, prior to imaging the breast, emitting a threshold signal when the applied force is within a first predetermined threshold of the target force. In another example, the method further includes, prior to imaging the breast, emitting a target signal when the applied force is within a second predetermined threshold of the target force. In yet another example, at least one of the threshold signal and the target signal includes at least one of a visual signal and an audible signal. In still another example, at least one of the threshold signal and the target signal includes a control signal for controlling a compression arm of the breast imaging system. In another example, the method further includes applying tactile feedback during manual compression based at least in part on the target force.

In another aspect, the technology relates to a method of guiding compression of a breast of a patient with a breast imaging system, the method including: obtaining an x-ray area of the breast of the patient; calculating a target force based at least in part on the x-ray area; and based at least in part on the calculation, sending a target force signal to a compression arm of the breast imaging system. In an example, the x-ray area is obtained from a storage device. In another example, the storage device is remote from the breast imaging system. In yet another example, the storage device includes at least one prior image of the breast of the patient and at least one prior image of another patient. In still another example, the x-ray area is obtained from a prior x-ray image of the breast of the patient.

In another example of the above aspect, when the prior x-ray image of the breast is unavailable, obtaining the x-ray area includes: receiving a distance measurement of a distance of a nipple of the breast from a chest wall of the patient; and estimating the x-ray area based at least in part on the received distance measurement. In an example, estimating the x-ray area includes comparing the distance measurement to a reference distance obtained from a reference. In still another example, obtaining the x-ray area is based on a size of a compression paddle.

In another aspect, the technology relates to a breast imaging system including: an x-ray source; a breast support platform; an x-ray detector disposed below the breast support platform; a compression arm disposed between the x-ray source and the breast support platform; a processor; a signal emitter connected to the processor; and memory storing instructions that when executed by the processor cause the breast imaging system to perform a set of operations including: obtaining an x-ray area of the breast of the patient, wherein the x-ray area is obtained from a prior x-ray image of the breast; comparing the x-ray area of the breast to a data set, wherein the data set relates the x-ray area of the breast to the target force; based at least in part on the comparison, identifying a target force; applying a compressive force to the breast with the compression arm, wherein the compressive force is based at least in part on the target force; and imaging the breast by emitting an x-ray energy from the x-ray source and receiving the x-ray energy at the x-ray detector. In an example, the set of operations further includes, prior to imaging the breast, emitting a threshold signal from the signal emitter when the applied compressive force is within a first predetermined threshold of the target force. In another example, the set of operations further includes, prior to imaging the breast, emitting a target signal from the signal emitter when the applied compressive force is within a second predetermined threshold of the target force. In yet another example, the signal emitter is at least one of an audio emitter and a visual emitter. In still another example, the signal emitter includes a display.

In another example of the above aspect, the x-ray area of the breast is based at least in part on a breast thickness. In an example, the set of operation further includes, applying tactile feedback during manual compression based at least in part on the target force.

DETAILED DESCRIPTION

Figure 1:
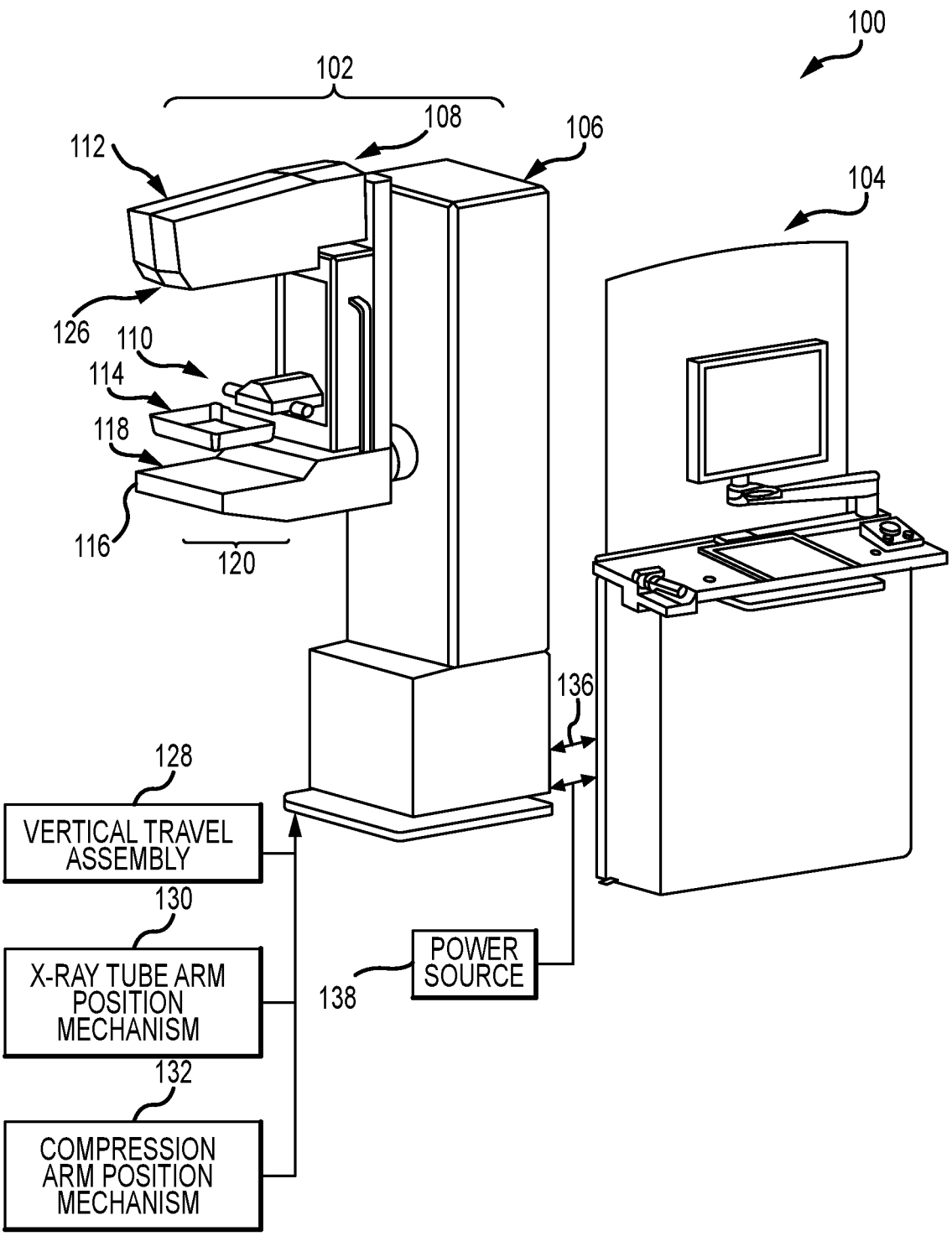
FIG. 1 is a perspective view of an example imaging system.

In various examples described herein, an imaging system is described that provides guidance for a healthcare professional to apply appropriate force to a patient's breast, to reduce compression variability by healthcare professionals, and to guide healthcare professional to maintain compression forces that match population based compression for breasts of similar area and thickness. The systems depicted in FIGS. 1-2B may be used to image a breast after the breast has been compressed with the compression paddle. The force applied, however, is often inconsistently applied for a number of reasons. This may be due to inexperience of the technologist, or a tendency of technologists (even experienced ones) to overcompress a breast, as many technologists are susceptible to the assumption that the breast must be compressed as much as possible for proper imaging. Too much compression, however, can lead to discomfort for the patient, which may cause them to avoid future breast imaging procedures.

Imaging system manufacturers have attempted to address these issues of inconsistent force application in a number of ways. In one example solution, breast compression is performed automatically, and the applied force on the breast and the resulting thickness are continually monitored. It is known that as the force increases, at some point the compressed breast thickness stops decreasing and a continual increase in force will not lead to further thickness changes. A cessation of further thickness changes may be automatically detected and compression terminated. However, technologists report that they do not feel in control of the compression by using this automated method.

In another example method, the optimal breast compression is determined to occur at a particular pressure, e.g., 75 mm Hg. In a standard mammography system, however, only the applied force is known; to calculate applied pressure, the cross-sectional area of the breast must also be known. This area can be determined by using a special paddle that measures the area of the breast that is in contact with the paddle, in real time. From the breast area and the applied force, the pressure is calculated, and visual feedback is given to the technologist when the target pressure of 75 mm Hg is reached. Disadvantages of this method include the use of a special paddle with sensors that is very expensive, and the method does not take into account any variation in compression pressure that might depend on compressed breast thickness.

Yet another known method relies on the known relationship between breast dimensions and force. For example, it is known that the visible area of the breast when placed under a compression paddle is roughly related to the distance that the nipple extends from the chest wall. A technologist may enter a nipple distance into the system and the breast area may be estimated therefrom. From the breast area and a particular compression pressure, e.g., 75 mm Hg, one may calculate the target compression force which can be displayed by the system and used by the technologist to guide her compression. One disadvantage of this method is that it requires that the technologist to perform the extra step of measuring the nipple extent and entering the value into the mammography system.

The technologies described herein provide guidance for a technologist on the proper force to apply to a given breast without the disadvantages of the systems and methods noted above. This reduces compression variability between technologists and procedures. The guidance may be based on the x-ray area of a patient breast (e.g., from a prior x-ray), or may be based on a estimation of the x-ray area (e.g., which can then be compared to a data set, such as a population data set). The technologies guide technologists to maintain compression forces that match population-based compression criteria for breasts of similar area and thickness. The technologies further reduce outlier compression forces (either too little compression resulting in poor image quality, or too high compression that increases patient discomfort) by instead providing a guidance force based on historical data for an individual patient or for breasts or patients having similar characteristics or criteria. The technologies accomplish this with no need for paddles with special sensors that typically measure forces applied to the surface of the breast, or for automated systems outside the control of the technologist. The guidance provided by the technologies described herein may further include visual or audio guidance, or tactile feedback, directed to the technologist who may be manually manipulating the system to apply pressure.

FIG. 1 is a perspective view of an example imaging system 100. In the example, the imaging system 100 may include a gantry 102 and a data acquisition work-station 104. The gantry 102 includes a housing 106 supporting a tube arm unit 108 that includes a rotatable compression arm assembly 110 and a rotatable x-ray tube assembly 112. The compression arm assembly 110 enables a patient's breast to be immobilized for x-ray imagining, such as either, or both, of mammography and tomosynthesis. The compression arm assembly 110 includes a compression paddle 114 and a receptor housing 116 disposed opposite the compression paddle 114. The receptor housing 116 has a compression surface 118 that directly contacts the breast during compression and immobilization. The receptor housing 116 encloses a detector subsystem 120 that includes an image receptor 122 and may include a retractable anti-scatter grid 124 (both shown in FIGS. 2A and 2B). The compression arm assembly 110 is in a path of an imaging beam that emanates from an x-ray source 126 housed in the x-ray tube assembly 112, such that the beam impinges in the image receptor 122.

The housing 106 may also house and enclose a vertical travel assembly 128 for moving the tube arm assembly 108 up and down to accommodate a particular patient or imaging position. An x-ray tube arm position mechanism 130 to rotate and/or position the x-ray tube assembly 112 for different imaging positions. A compression arm position mechanism 132 to rotate and/or position the compression paddle 114, image receptor 122, and the grid 124. Generally, the housing 106 includes any suitable motors and electrical and mechanical components and connections to implement these functions as discussed herein.

The work-station 104 may include a display screen (typically a flat panel display that may include touch-screen functionality), user interface devices such as a keyboard, a mouse or trackball, and various switches and indicator lights and/or displays. The work-station 104 also includes computing facilities (e.g., hardware, firmware, and software) for controlling the gantry 102 and for processing, storing, and displaying data and images received from the gantry 102 during imaging operations. The gantry 102 and the work-station 104 may exchange data and controls of a schematically illustrated connection 136. In other examples, the gantry 102 and the work-station 104 may be integration in a single unit. A power source 138 may power the imaging system 100.

Figure 2A:
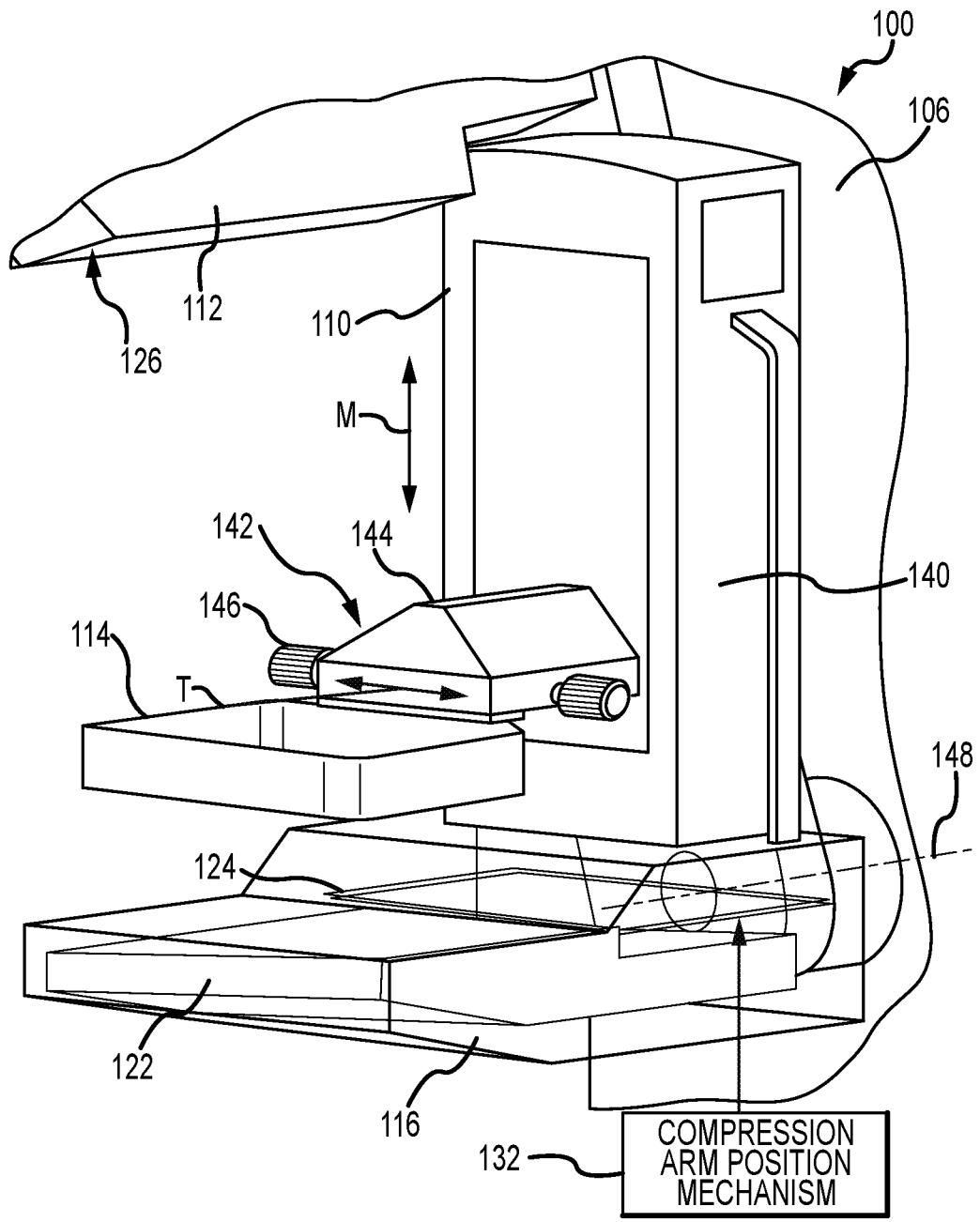
FIG. 2A is a partial enlarged view of the imaging system of FIG. 1.
Figure 2B:
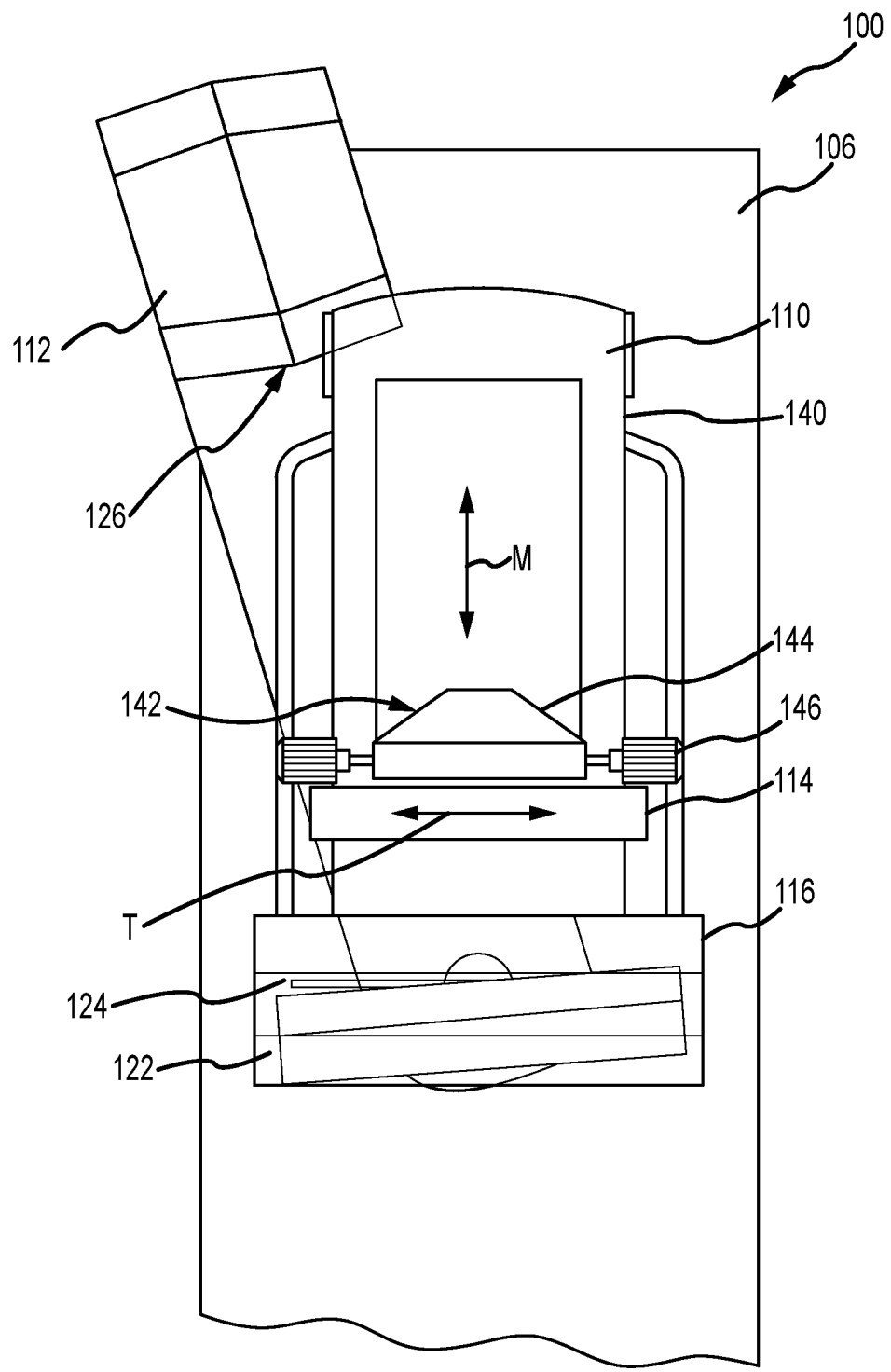
FIG. 2B is a partial front view of the imaging system of FIG. 1.

FIG. 2A is a partial enlarged view of the imaging system 100 of FIG. 1. FIG. 2B is a partial front view of the imaging system 100. Referring concurrently to FIGS. 2A and 2B, certain components of the imaging system of FIG. 1 are described above, and as such, are not necessarily described further. In operation, the imaging system 100 immobilizes a patient's breast for x-ray imaging (either or both of mammography and tomosynthesis) via the compression arm assembly 110 that includes the static receptor housing 116 and the moveable compression paddle 114, both which are coupled to a support arm 140. The compression paddle 114 is configured to move M along the support arm 140 and toward the receptor housing 116 to compress and immobilize the breast. The compression paddle 114 is positionable and supported by a compression arm device 142 that is disposed at least partially within the support arm 140 and at least partially outside of the support arm 140. In some examples, the compression paddle 114 may also be configured to linearly translate T in relation to the compression arm device 142. The compression arm device 142 includes an external compression device assembly 144 that the compression paddle 114 can removably couple thereto. The compression device assembly 144 includes at least one rotatable knob 146, which can be utilized to move the compression paddle 114 as described herein. In the example, the compression arm device 142 may be a component of the compression arm position mechanism 132 (shown in FIG. 2A) that drives motion of the compression paddle 114.

For mammography, the compression arm assembly 110 and the x-ray tube assembly 112 can rotate as a unit about an axis 148 (shown in FIG. 2A) between different imaging orientations such as CC and MLO, so that the imaging system 100 can take a mammogram projection image at each orientation. In mammography imaging operations, the image receptor 122 remains in place relative to the receptor housing 116 while an image is taken. The compression arm assembly 110 can release the breast for movement of one or more of the compression arm assembly 110 and the x-ray tube assembly 112 to a different imaging orientation. For tomosynthesis, the compression arm assembly 110 stays in place, with the breast immobilized and remaining in place, while at least the x-ray tube assembly 112 rotates the x-ray source 126 relative to the compression arm assembly 110 and the compressed breast about the axis 148. The imaging system 100 takes plural tomosynthesis projection images of the breast at respective angles of the x-ray beam relative to the breast.

Concurrently and optionally, the image receptor 122 may be tilted relative to the receptor housing 116 and coordinated with the rotation of the x-ray tube assembly 112. The tilting can be through the same angle as the rotation of the x-ray source 126, but may also be through a different angle selected such that the x-ray beam remains substantially in the same position on the image receptor 122 for each of the plural images. The tilting can be about the axis 148, which can, but need not, be in the image plane of the image receptor 122. The compression arm position mechanism 132 can drive the image receptor 122 in a tilting motion. For tomosynthesis imaging and/or CT imaging, the receptor housing 106 can be horizontal or can be at an angle to the horizontal, e.g., at an orientation similar to that for conventional MLO imaging in mammography. The system 100 can be solely a mammography system, a CT system, or solely a tomosynthesis system, or a "combo" system that can perform multiple forms of imaging.

When the system is operated, the image receptor 122 produces imaging information in response to illumination by the imaging x-ray beam from the x-ray source 126, and supplies it to an image processor of the work-station 104 (shown in FIG. 1) for processing and generating breast x-ray images. The work-station 104 may control the operation of the imaging system 100 and interacts with the health professional to receive commands and deliver information including processed x-ray images.

One challenge with the imaging system 100 is how to immobilize and compress the breast for the desired or required imaging without causing undue discomfort to the patient. A health professional, typically an x-ray technologist, generally adjusts the breast within the compression arm assembly 110 while pulling tissue towards imaging area and moving the compression paddle 114 toward the receptor housing 116 to immobilize the breast and keep it in place, with as much of the breast tissue as practicable being between the compression paddle 114 and receptor housing 116.

Figure 3:
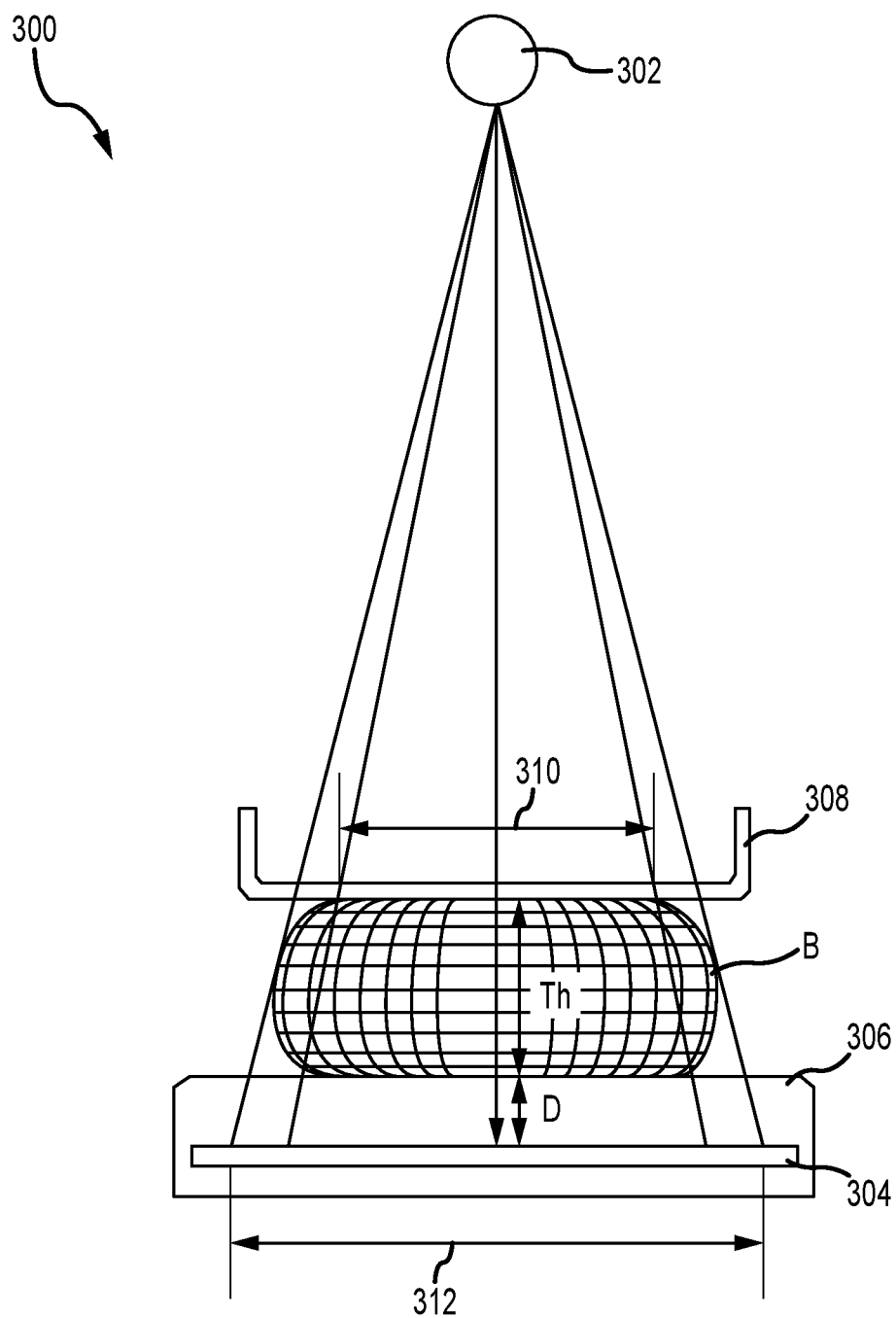
FIG. 3 depicts a partial view of a compression assembly of a breast imaging system.

The technologies described herein are based on the discovery that further force applied to a breast does little to further compress the breast; rather, discomfort is simply increased. It has been determined that, from a significant sample of breasts of a particular population, a target guidance force may be determined, and this target force may be applied across patients in a similar population, so as to apply a consistent force to all patients. As force is applied to a breast, the breast compresses to an image area; that is, the area of the breast as it appears in a mammogram image. This image area, and an explanation of other areas, is depicted relative to a compression assembly 300 depicted in FIG. 3. Relevant parts of the compression assembly 300 include an x-ray source 302 and an x-ray detector 304. The detector 304 is disposed below a breast support platform 306 and supports a breast B a distance D above the x-ray detector 304 (an anti-scatter grid is not shown). A breast compression paddle 308 compresses the breast B during imaging procedures. FIG. 3 depicts a breast contact area 310 which is defined by the portion of the breast B that contacts the compression paddle 308. This contact area 310 can be notoriously difficult to accurately measure, since it requires a number of sensors disposed on or in the compression paddle 308 to detect contact between the breast B and the compression paddle 308. These sensors may also produce artifacts in the generated x-ray image, which may interfere with analysis of the image. FIG. 3 also depicts an x-ray image area 312, which corresponds to the area of the breast B as projected on the detector 304. This area 312 is significantly easier to measure, e.g., by counting the number of pixels between a chest wall of the patient and a skin line of the breast in the image. Invariably, the x-ray image area 312 is larger than the contact area 310, due to the curved shape of the compressed breast. The x-ray image area is also larger than the true x-ray breast area due to geometric magnification which depends upon the breast thickness Th.

Figure 4:
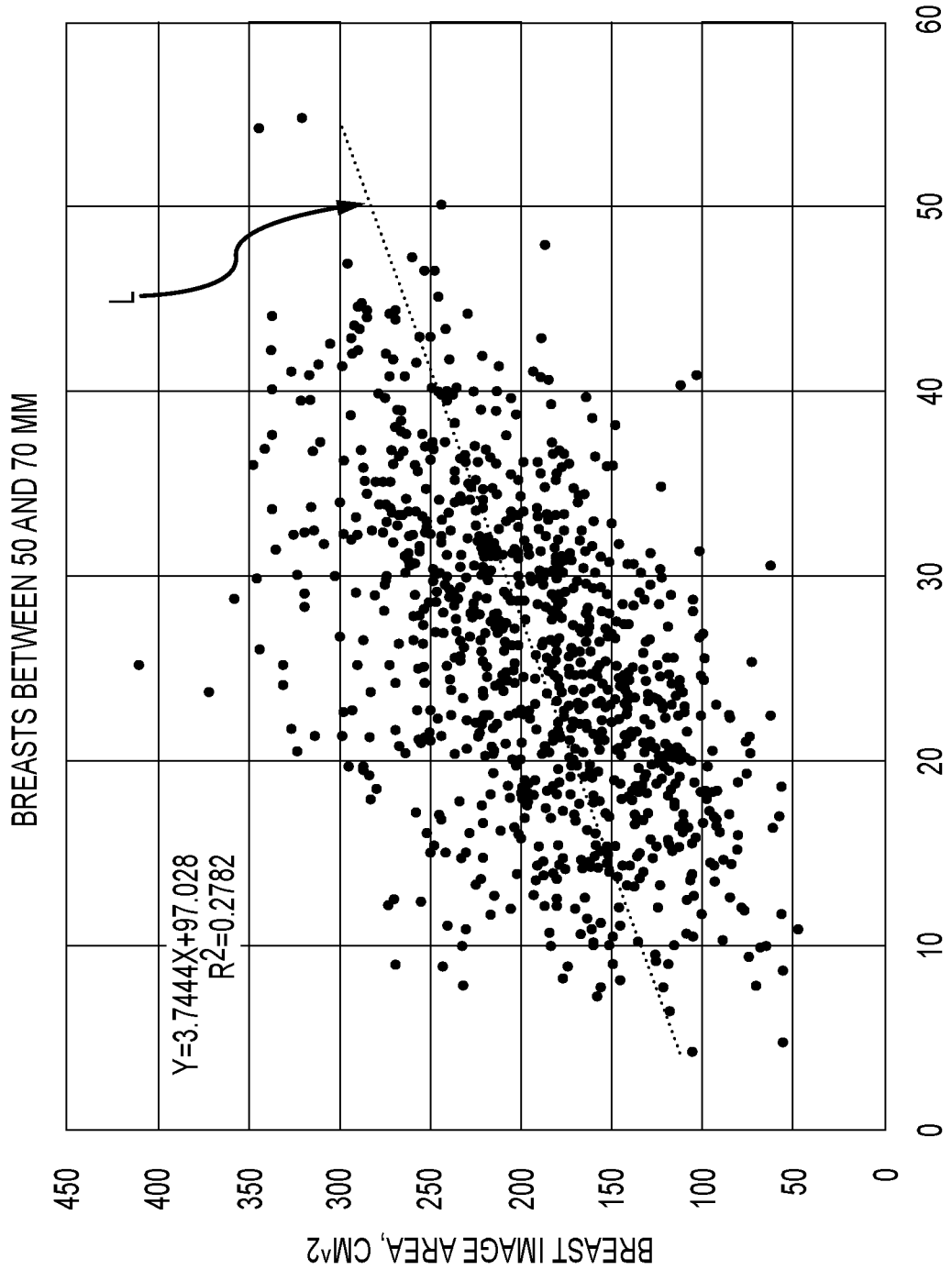
FIG. 4 depicts an example plot of a historical data set for breast image area versus force applied.

To maintain consistent force application across patients of a particular population, a median force that has been observed to be historically delivered to breasts of similar characteristics should be calculated. Some examples of breasts with similar characteristics are breast area and/or breast thickness and/or breast density. To do so, historical mammogram data in a population is first collected. The population may be characterized by similarities in patient geographic location, age, breast density, or other criteria. In examples, this collection may take place during product development, or during other controlled testing performed by highly specialized persons to achieve extremely high-quality images. A large database of mammograms may be collected and may be quality-controlled so that the database contains high-quality mammograms from systems operating properly. From this database, data may be generated that provides information on the relationship between applied compression force and x-ray image area. An example of this is shown in FIG. 4. A fit (depicted by line L) between the area and the force may also be determined using an algorithm.

With the historical mammogram data known, the guidance force for a breast to be imaged may be calculated based on its known projection area. In this example, assuming that the measured projection area was 200 cm$^2$, then using the data in FIG. 4, the average force is approximately 27.5 lb=(200-97.028)/3.7444. This guidance force corresponds to the average force in the database, but median force, or some larger or smaller factor (e.g., less than one) may be utilized to adjust the guidance force. The guidance force may be applied by the compression arm as a target force, which the compression arm will attempt to apply to the breast prior to an imaging procedure. The terms "guidance force" or "target force" is used because in some imaging systems, the technologist may still adjust the force applied to the breast (e.g., if a resulting x-ray image is not diagnostically relevant, or to reduce force applied to breasts of a woman that are particularly sensitive).

In the example, an x-ray image area of a previous x-ray image of the patient's breast may be obtained so as to compare to the historical mammogram data and identify the target force. However, a previous x-ray image of the patient's breast may not be available. If the previous x-ray image is unavailable, the image area of the breast may be estimated. One reason previous or prior images may not be available may be that the patient is obtaining a mammogram for the first time, or the imaging system is not connected to a database having access to the patient's prior records. One method of estimating the image area is by measuring a distance from the nipple of the breast to the chest wall. This distance may be compared to nipple reference data, for example from a similar population of patients, to obtain an estimate of the breast x-ray image area. The nipple reference data may form a part of the historical mammogram data referenced above, such that a nipple measurement corresponds to a breast x-ray image area, as well as to a guidance force. In one example, by using a breast size estimate and historical mammogram data that includes nipple reference data as an alternative to obtaining x-ray image area from the previous x-ray image, there is at all times a way to determine the image area.

Figure 5:
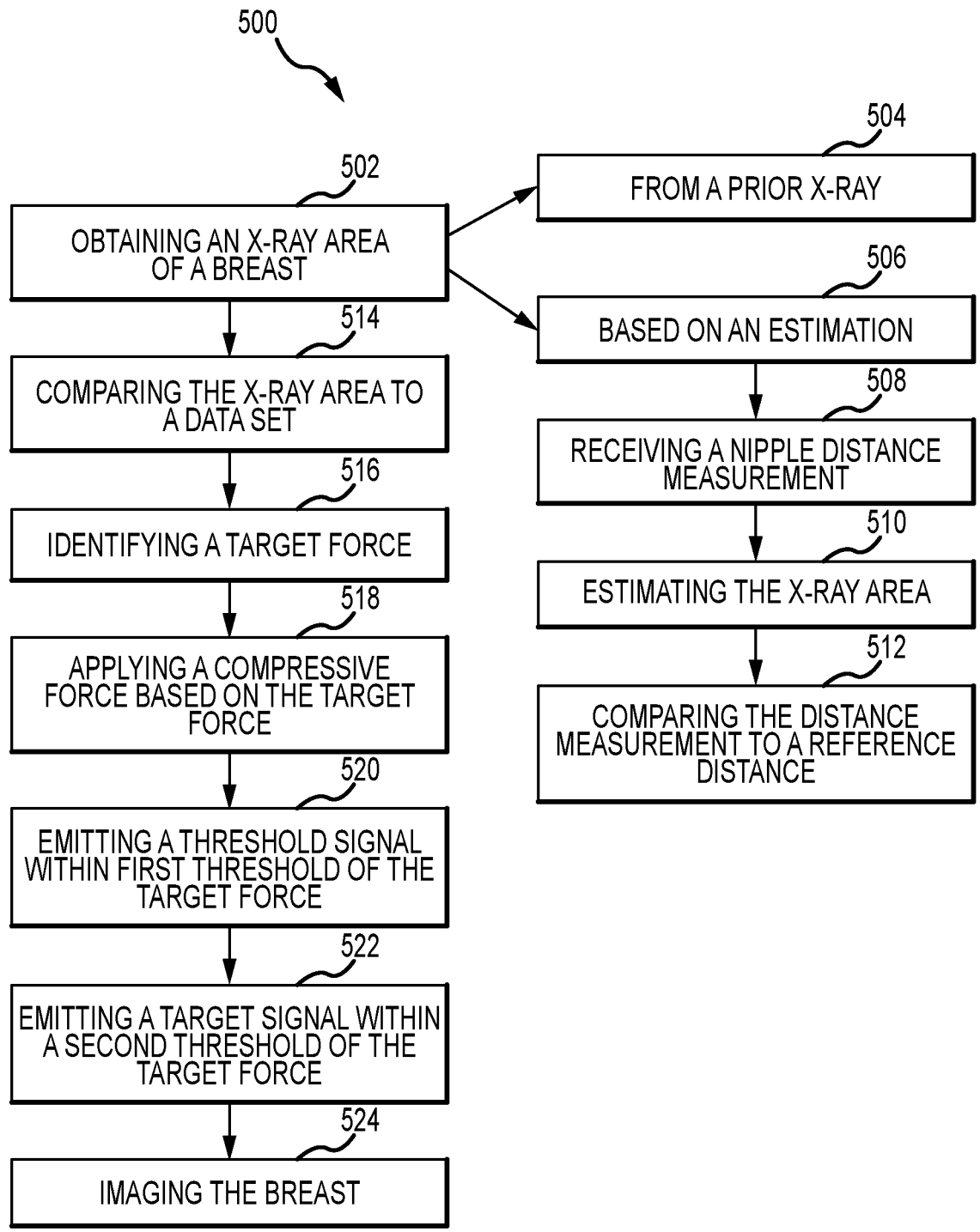
FIG. 5 depicts a method of compressing a breast of a patient with a breast imaging system.

With these initial considerations in mind, FIG. 5 depicts a method 500 of compressing a breast of a patient with a breast imaging system such as imaging system 100 described above. The method 500 begins with obtaining an x-ray area of the breast of the patient, operation 502. As noted above, this may be obtained from a prior x-ray of the breast, operation 504. In an aspect, obtaining x-ray area from a prior x-ray may be performed by measuring (e.g., counting pixels) distance between a chest wall of the patient and a skin line of the breast in the prior x-ray image. However, a previous x-ray image of the patient's breast may not be available. As such, when the previous x-ray image of the patient is unavailable, the x-ray area may be obtained based on an estimation, operation 506. The estimation, in one example, requires an input of a measurement of the distance from the chest wall to the nipple. This measurement may be performed manually, e.g., by the technologist as part of the preparation for the imaging procedure. Alternatively, the measurement may be performed automatically, using cameras and image recognition and measurement software to measure the distance. The distance may be measured when the breast is resting on the support platform and the breast may be uncompressed or just slightly compressed (e.g., to stabilize the breast for the measurement). This nipple distance measurement is then received, operation 508, and the x-ray area is estimated based on the distance, operation 510. In examples, the estimation may be performed by comparing the nipple distance measurement to nipple reference data, operation 512. The nipple reference data may form a part of a historical mammogram data set that includes nipple distance, corresponding area information, and an associated applied force that may be used in other operations of the method 500.

In another example, estimation of the x-ray area may be based on bra cup size of the patient. For example, bra cup size may be input by the technologist, and then based at least partially on the input information of cup size, x-ray area can be estimated. In an aspect, the estimation may be performed by comparing cup size to cup reference data so as to obtain an estimated x-ray area. The cup reference data may form a part of the historical mammogram data set as required or desired.

At operation 514, the x-ray area is compared to a data set, such as the historical mammogram data described above. In an aspect, the data set includes x-ray image area values and applied compression force values collected for one or more characterized patient groups and from x-ray images (e.g., geographic location, age, breast density, breast thickness, nipple distance, cup size, etc.). The data set may be stored on the imaging system, at a remote workstation (such as depicted in FIG. 1), or in a network storage system of an imaging clinic or hospital in which the imaging system is located. In still other examples, the data set may be stored remotely at an imaging system manufacturer. Thus, the manufacturer may continue to update the data set based on other high-quality images and measurements that may be obtained during testing. The data set may include a look-up table that may associate a particular x-ray image area with a guidance or target force, which may be obtained from a population similar to the patient, as described above. In another example, the x-ray area may be applied to an algorithm generated from the data set. Thus, based on the x-ray image area and the information available from the data set, a target force may be identified, operation 516. Thereafter, a compressive force may be applied to the breast, operation 518. This compressive force is based at least in part on the target force. The compressive force may be applied to the breast either by manual manipulation of a knob or button on the imaging system, or automatically by one or more motors or a combination thereof. For example, where the compressive force is partially applied automatically to a particular point, and then can manually be applied by a manipulation of a knob. The target force is not immediately applied; rather, the force applied to the breast is increased incrementally towards the target force.

As the applied force approaches the target or guidance force, a guidance signal may be sent to either control or guide the further application of force to the breast. Multiple guidance signals may be sent, as required or desired for a particular application, and the guidance signals may be in the form of visual or audible signals emitted from the imaging system, or control signals sent to the components of a compression arm (e.g., a motor). Using audible and visual signals illustratively, multiple thresholds may be utilized as the compression force approaches the target force. For example, as the technologist rotates a knob to apply force to the breast, as the force reaches a first threshold (e.g., within 30%, 25%, 20%, or less of the target force), a threshold signal in the form of a chime or sound may be emitted, or a visible light may be illuminated, operation 520. This indicates to the technologist that the force is increasing and may signal the technologist to inquire with the patient as to her comfort level. The technologist may further be trained to begin to slow rotation of the knob, to as to reduce the rate of force application. As the applied force reaches a second threshold (e.g., 10%, 5%, or less), a target signal may be emitted, operation 522. The target signal may be distinguished from the threshold signal based on at least one of sound volume, a sound tone or type, a light brightness or color, a light emission pattern, etc. This guides the technologist to further reduce or stop application of additional force to the breast. In other examples, the guidance signal may be in the form of one or more control signals sent to operative components of the compression arm, to slow or stop rotation of a motor used to actuate the compression arm. Once the target force is reached (or once further application of compressive force is terminated, due to technologist discretion, for example), imaging of the breast may be performed, operation 524.

Furthermore, in some examples, the target force identified from the data set may be further refined based on breast thickness measured during the breast immobilization procedure. In an aspect, if x-ray area is estimated, once the compression paddle initially touches the patient's breast, breast thickness may be measured via a thickness sensor on the image system, and this information may be used to further adjust the target force. For example, a thicker breast may require more compression force than a thinner breast with a similar x-ray area. To determine when the compression paddle initially touches the patient's breast, the applied compression force of the paddle may be monitored and a spike in force can correspond to the initial touch of the paddle with the patient. In another aspect, if a prior image of the patient is used for the x-ray area, breast thickness may be measured as feedback for the applied force as the target force is being approached. As such, along with historical x-ray area and compression force data, breast thickness data is stored and accessible for use as described herein.

Additionally, or alternatively, the guidance signal may be used to control the speed of the compression arm during application of the target force. For example, the compression arm may slow as the compression paddle approaches the patient's breast. Slowing movement of the components of the imaging system can increase patient comfort. In another example, the compression arm may slow even further once compression of the patient's breast begins with the compression paddle. In these examples, the speed of the compression arm may be at least partially based on the compression force of the compression arm, such as, moving at a first speed prior to compression force being exerted and then slowing towards a second speed once compression force begins. Accordingly, the compression arm gradually compresses the patient breast so as to increase patient comfort.

Figure 6:
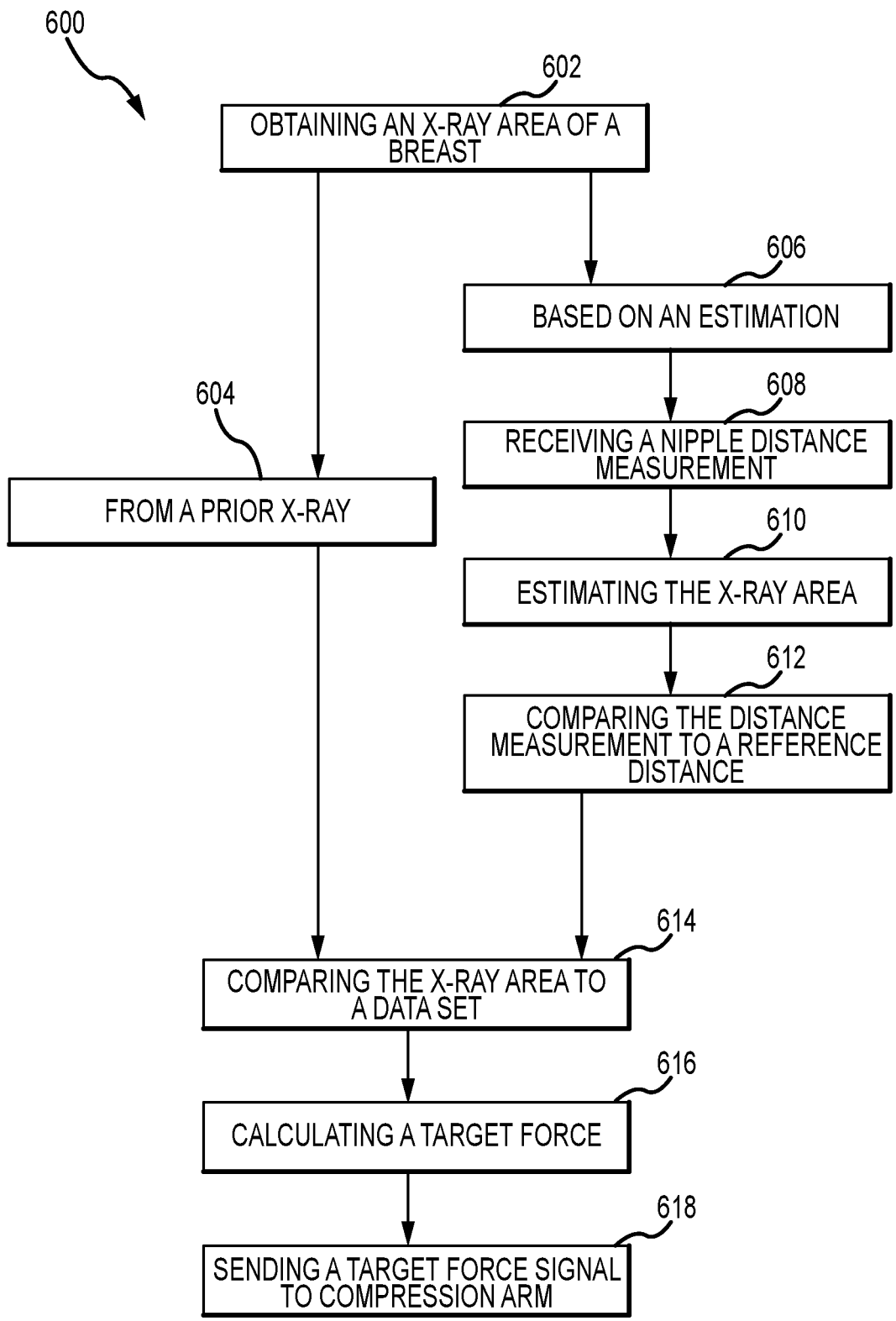
FIG. 6 depicts a method of guiding compression of a breast of a patient with a breast imaging system.

FIG. 6 depicts a method 600 of guiding compression of a breast of a patient with a breast imaging system, which begins with obtaining an x-ray area of the breast of the patient, operation 602. This may be obtained, in one example, from a prior x-ray of the breast, operation 604. In an aspect, the pixels between a chest wall and a skin line within the prior x-ray may be counted so as to obtain the x-ray area. However, use of a prior x-ray may not be available. If a prior x-ray is not available, the x-ray area may be obtained based on an estimation, operation 606. The estimation requires an input of a measurement of the distance from the chest wall to the nipple. This measurement may be performed manually or automatically, as noted above. This nipple distance measurement is then received, operation 608, and the x-ray area is estimated based on the distance, operation 610. In examples, the estimation may be performed by comparing the nipple distance measurement to nipple reference data, operation 612. The nipple reference data may form a part of a historical mammography data set that includes nipple distance, corresponding area information, and an associate applied force that may be used in other operations of the method.

At operation 614, the x-ray area is compared to a data set, such as the historical mammography data described above. In an aspect, the data set includes x-ray image area values and applied compression force values collected for one or more characterized patient groups and from x-ray images (e.g., geographic location, age, breast density, breast thickness, nipple distance, cup size, etc.). The data set may be stored on the imaging system, at a remote workstation (such as depicted in FIG. 1), in a network storage system of an imaging clinic or hospital in which the imaging system is located remotely at an imaging system manufacturer. The x-ray area may be applied to an algorithm, such that generated from the data set. A target force may be calculated, operation 616. Thereafter, a target force signal is sent to a compression arm, operation 618. Further guidance signals, such as described above, may also be emitted as required or desired for a particular application.

Figure 7:
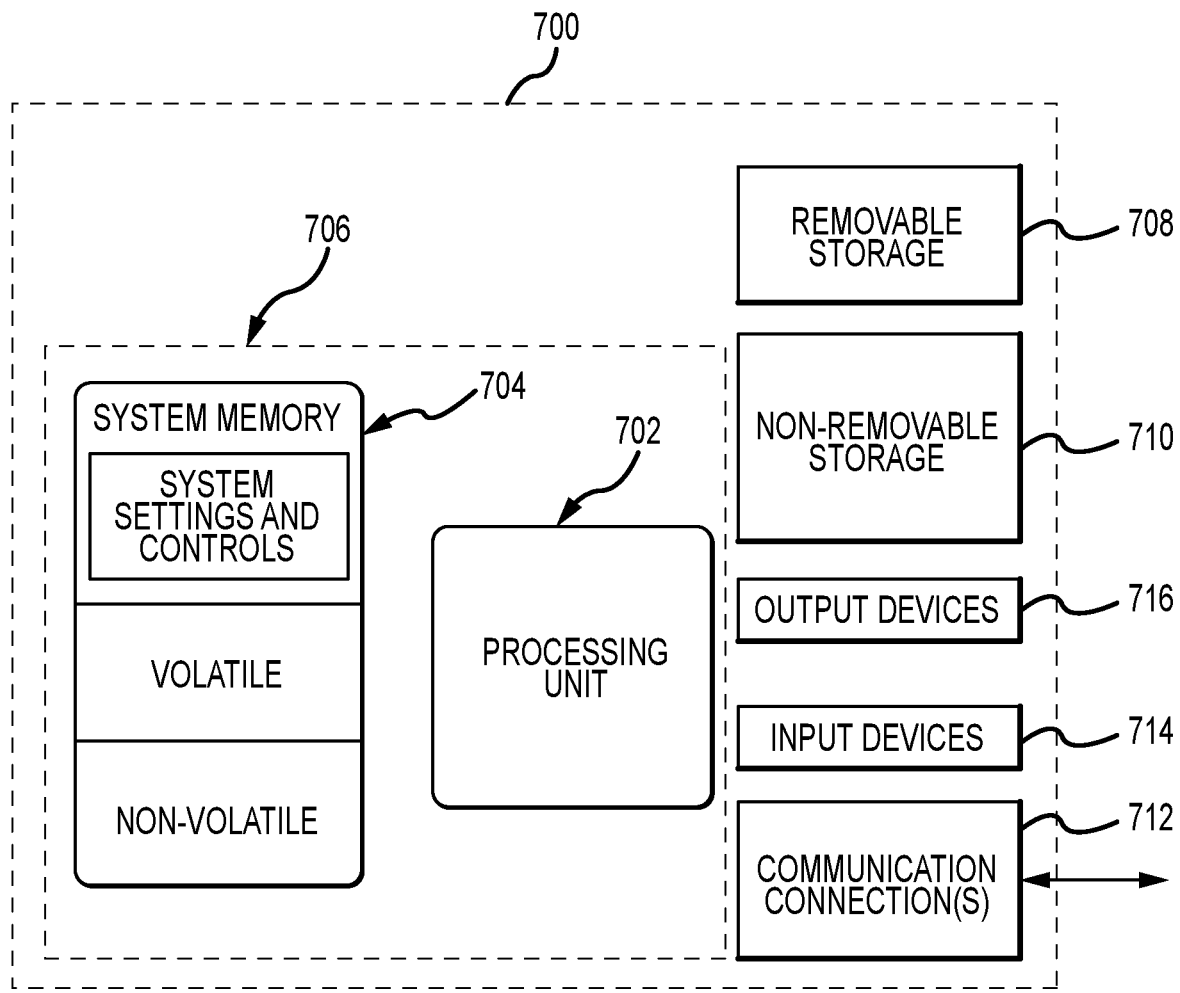
FIG. 7 depicts an example of a suitable operating environment in which one or more of the present examples can be implemented.

FIG. 7 depicts one example of a suitable operating environment 700 in which one or more of the present examples can be implemented. This operating environment may be incorporated directly into the controller for a breast imaging system, e.g., such as the controller depicted in FIG. 1. This is only one example of a suitable operating environment and is not intended to suggest any limitation as to the scope of use or functionality. Other well-known computing systems, environments, and/or configurations that can be suitable for use include, but are not limited to, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 700 typically includes at least one processing unit 702 and memory 704. Depending on the exact configuration and type of computing device, memory 704 (storing, among other things, instructions to control the compression arm, image of the breast, or perform other methods disclosed herein) can be volatile (such as RAM), non-volatile (such as ROM, flash memory, etc.), or some combination of the two. This most basic configuration is illustrated in FIG. 7 by dashed line 706. Further, environment 700 can also include storage devices (removable, 708, and/or non-removable, 710) including, but not limited to, magnetic or optical disks or tape. Similarly, environment 700 can also have input device(s) 714 such as touch screens, keyboard, mouse, pen, voice input, etc., and/or output device(s) 716 such as a display, speakers, printer, etc. Also included in the environment can be one or more communication connections 712, such as LAN, WAN, point to point, Bluetooth, RF, etc.

Operating environment 700 typically includes at least some form of computer readable media. Computer readable media can be any available media that can be accessed by processing unit 702 or other devices having the operating environment. By way of example, and not limitation, computer readable media can include computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media. A computer-readable device is a hardware device incorporating computer storage media.

The operating environment 700 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

In some examples, the components described herein include such modules or instructions executable by computer system 700 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some examples, computer system 700 is part of a network that stores data in remote storage media for use by the computer system 700.

As described above in reference to FIG. 5, the compressive force that is applied to the breast is based at least in part on the identified target force. In some examples, this target compression force is performed by manual manipulation of a knob on the imaging system (e.g., the knob 146 shown in FIG. 2A). In addition to, or alternatively from, the audible and visual signals provided to the technologist, the knob may provide tactile feedback to the technologist based on the position of the paddle relative to the identified target force. In an aspect, tactile feedback of the knob may be in the form of torque resistance so that the closer to the identified target force the position of the paddle is, the more resistance is provided on the knob. Torque resistance may be selectively applied by either a mechanical system or an electronic system as required or desired. In an aspect, the tactile feedback is included in the compression arm position mechanism 132 (shown in FIG. 1).

In some imaging systems, the torque resistance applied to the knob can be based on an upper limit of compression force in the system. As such, the technologist may develop a feel for approximately how much compressive force is being applied by the paddle based on the resistance of the knob. However, the identified target force is often below the upper limit of the system. As such, the technologist may continue to overcompress the patient's breast because the lower compression force based on the target force may not "feel" normal when performing manual compression. In this example, the system may base the tactile feedback of the knob on the identified target force. Accordingly, the knob will have a similar torque resistance applied during paddle positioning to reach the identified target force. By adjusting tactile feedback for the technologist, compression variability is reduced, imaging performance is increased, and patient comfort is increased.

In the example, by basing the torque resistance applied to the knob on the identified target force, as the technologist positions the paddle, the torque resistance will feel similar during all compression procedures as the force applied to the breast is increased towards the target force even though the target force can be different for different patients. For example, if a higher target force is identified, then the paddle may need to be positioned closer to the support platform than if a lower target force is identified. As such, when the force applied to the breast is at 50% of the target force, the force being applied will be different for the higher and lower values, but the torque resistance will be similar on the knob. Thus, the technologist can keep a "feel" for how much compression is being applied to the breast, but the resistance is now being based on the identified target force as described above.

The tactile feedback in the system may include a look-up table that may associate a particular compression value with a torque resistance. In an aspect, the torque resistance may be related to the percent of the target force being applied so that all relative percent values (e.g., 50%, 75%, 90%) of the target force provide the same or similar torque resistance even while the target force changes for different patients. In other aspects, the torque resistance may be applied to an algorithm based on the target force.

Figure 8:
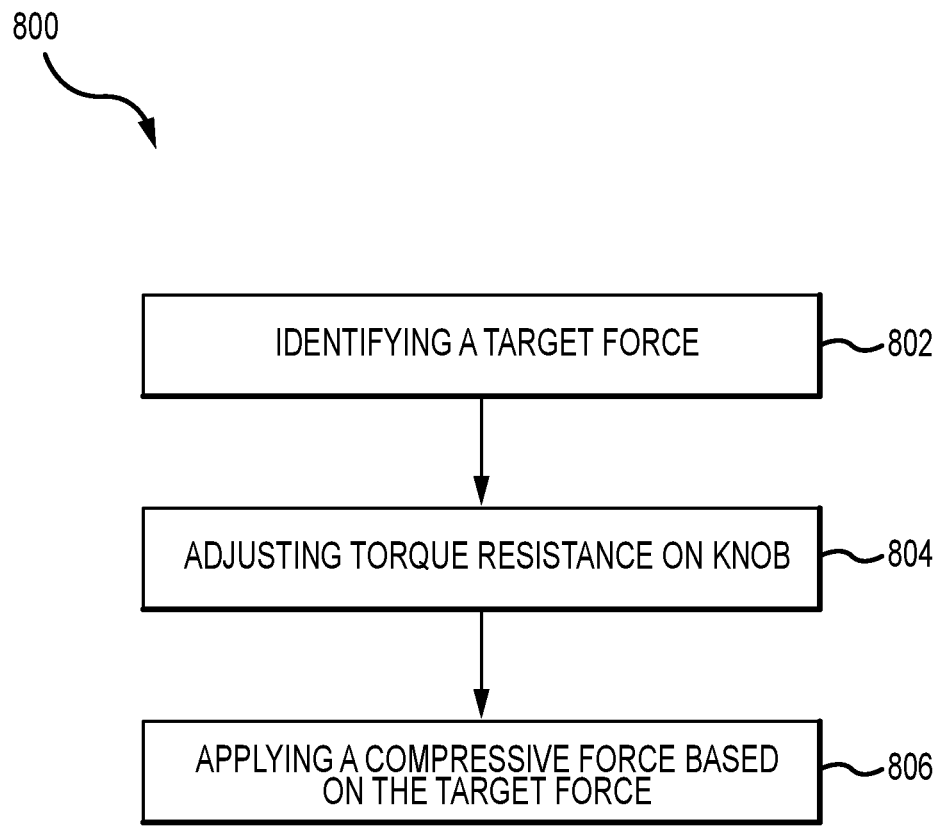
FIG. 8 depicts a method of applying tactile feedback during manual application of a compression force.

Turning now to FIG. 8, FIG. 8 depicts a method 800 of applying tactile feedback during manual application of a compression force. The method 800 begins with identifying a target force, operation 802, which is described in detail above. Once the target force is identified, the torque resistance of the manual knob is adjusted based on the identified target force, operation 804. For example, the torque resistance may be set to increase constantly towards the identified target force. This may be performed via a look-up table or algorithm and implemented mechanically or electronically as required or desired. As such, the feedback the technologist receives via the manual knob is based on the identified target force and not system set values. Thereafter, a compressive force may be manually applied to the breast via the knob, operation 806.

As described above in FIGS. 5 and 6, an x-ray area of the breast of the patient is obtained so as to identify the target force, and the area may be obtained from a prior x-ray of the breast or based on an estimation. In some aspects, for example, where neither a prior image nor an estimation is available or obtainable, the target force may be alternatively be identified based on a size of the compression paddle attached to the image system. Generally, smaller compression paddle sizes require less target force than larger compression paddles because the size of the compression paddle is typically selected based on patient breast size. While the identified target force based on paddle size may not be as accurate as the prior image or the estimation procedures described above, the identified target force based on paddle size will still reduce compression variability, increase imaging performance, and increase patient comfort when compared to not identifying any target force value.

Figure 9:
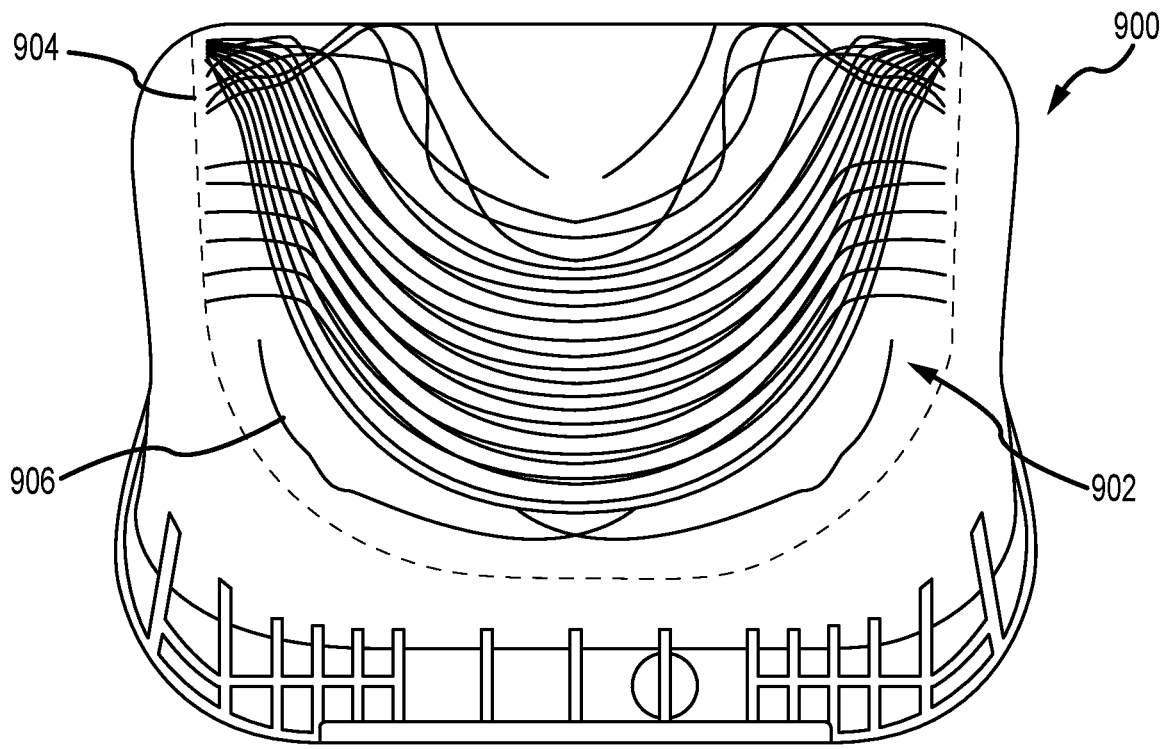
FIG. 9 is a bottom view of an exemplary large compression paddle.
Figure 10:
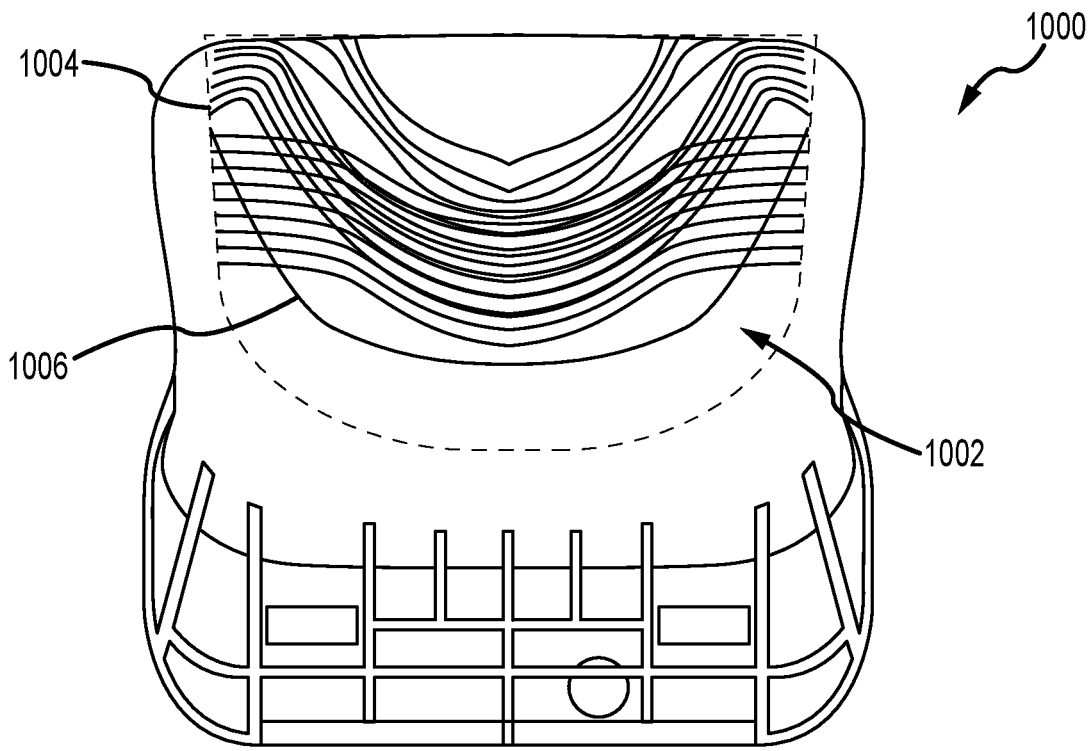
FIG. 10 is a bottom view of an exemplary small compression paddle.

FIG. 9 is a bottom view of an exemplary large compression paddle 900. FIG. 10 is a bottom view of an exemplary small compression paddle 1000. Referring concurrently to FIGS. 9 and 10, both paddles 900, 1000 have a compression surface 902, 1002 formed on a bottom wall and configured to face the compression surface 118 of the receptor housing 116 (both shown in FIG. 1) so that breast compression and/or immobilization occurs therebetween. The compression surface 902, 1002 is defined by a surface area 904, 1004 that is configured to contact the patient's breast. In the example, the surface area 904 of the paddle 900 is greater than the surface area 1004 of the paddle 1004. As such, the paddle 900 has a larger size than the paddle 1000, and generally, the paddle 900 is selected by the technologist for use with larger breasts and the paddle 1000 is selected by the technologist for use with smaller breasts. It is appreciated that while two different paddle sizes are shown herein, compression paddles are known to come in a wide variety of additional shapes and sizes. In examples, compression paddles may have a substantially flat compression surface, or may have a curved compression surface.

Because the compression paddle that the technologist selects corresponds to patient breast size, and the surface area 904, 1004 for each compression paddle is known and measurable, the target force identified by the image system can be based on the compression paddle size. In examples, the image system may store compression paddle data (e.g., paddle type and surface area) that is automatically accessible once a compression paddle is attached to the image system and identified. Thus, the imaging system knowing the surface area of the compression paddle and a required or desired compression pressure, can calculate the target force for breast compression and use this target force during imaging procedures.

As further illustrated in FIGS. 9 and 10, a plurality of breast perimeter outlines 906, 1006 are shown. These outlines 906, 1006 represent breast position relative to the compression surface area 904, 1004 for a number of different breasts over different imaging procedures. These outlines may be collected as data on the imaging system, at a remote workstation, or in a network storage system of an imaging clinic or hospital in which the imaging system is located. In other examples, the outline data may be stored remotely at an imaging system manufacturer. Similar to the databases described above, breast outline information may be stored in a database for access, quality control, and/or analyzing relationships and algorithms. As shown in FIGS. 9 and 10, actual breast position relative to the surface area 904, 1004 may not completely fill the area. As such, to further refine the target force calculated based on compression paddle size, the surface area 904, 1004 may be reduced by a predetermined amount prior to calculating the target force. By further adjusting the surface area 904, 1004 based on actual use conditions of the compression paddle, the calculated target force can further reduce compression variability, increase imaging performance, and increase patient comfort when compared to not identifying any target force value.

Starting with FIG. 9, the largest breast outlines 906 on the paddle 900 do not correspond to the entire surface area 904. As such, the surface area 904 may be reduced by a predetermined amount prior to calculating the target force. In the example, the predetermined amount is based on a largest breast outline 906 from the collected data. In other examples, the predetermined amount is based on a mean, median, or average breast outline 906. In still other examples, the predetermined amount may be based on a mean, median, or average of a top percentile of outlines (e.g., top 10%, top 25%, etc.). Accordingly, in an aspect, the surface area 904 may be reduced by 2-15% prior to calculating the target force. In another aspect, the surface area 904 may be reduced by about 5%. In yet another aspect, the surface area 904 may be reduced by about 10%.

Turning to FIG. 10, and similar to the large paddle 900, the largest breast outlines 1006 on the paddle 1000 do not correspond to the entire surface area 1004. As such, the surface area 1004 may be reduced by a predetermined amount prior to calculating the target force. In the example, the predetermined amount is based on a largest breast outline 1006 from the collected data. In other examples, the predetermined amount is based on a mean, median, or average breast outline 1006. In still other examples, the predetermined amount may be based on a mean, median, or average of a top percentile of outlines (e.g., top 10%, top 25%, etc.).

Accordingly, in an aspect, the surface area 1004 may be reduced by 2-25% prior to calculating the target force. In another aspect, the surface area 1004 may be reduced by about 10%. In yet another aspect, the surface area 1004 may be reduced by about 15%. As shown by FIGS. 9 and 10, the predetermined reduction amount for the surface areas 904, 1004 may be different for different paddle sizes.

Figure 11:
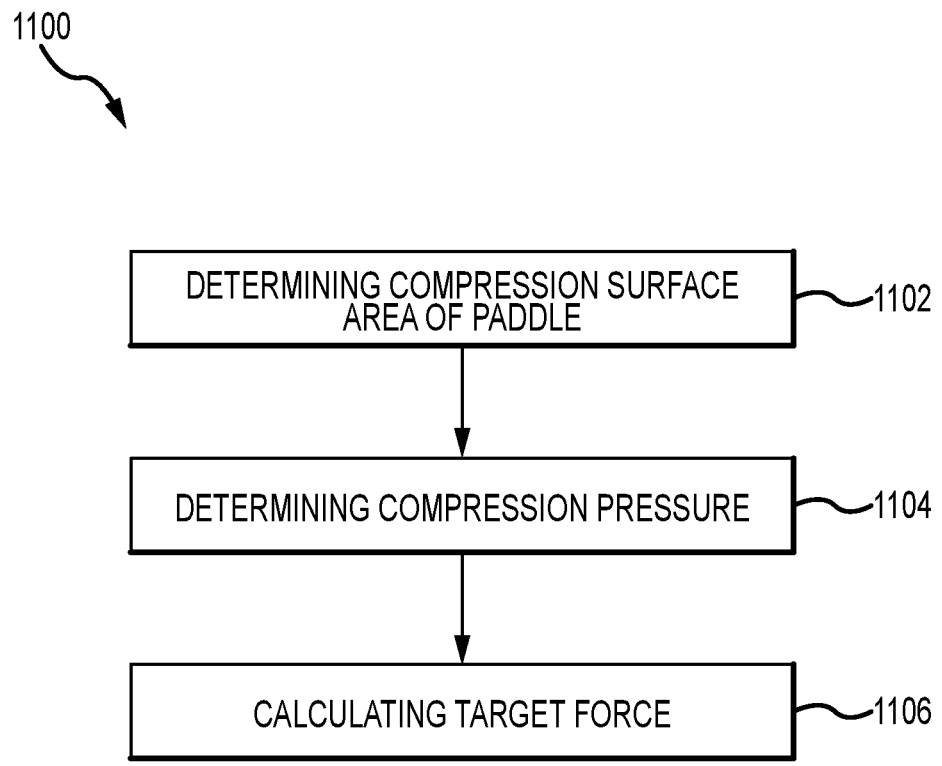
FIG. 11 depicts a method of calculating a target force based on paddle size.

FIG. 11 depicts a method 1100 of calculating a target force based on paddle size. The method 1100 begins with determining a compression surface area of a paddle, operation 1102. In some examples, the surface area information is saved in the image system and corresponds to the paddle attached thereto. By having data that allows for each different compression paddle that is usable in the image system to include information related to the compression surface area, once the paddle is attached to the system, the paddle can be automatically identified and the information regarding the surface area accessible. In some examples, the compression surface area may be modified by a predetermined reduction amount to account for breasts not typically occupying the entire compression surface area during imaging procedures. Additionally, a required or desired compression pressure is determined, operation 1104. Demining compression pressure may be an input from the technologist or be based on preset or historical data that relates compression pressure to compression and/or immobilization performance for imaging. In an aspect, the compression pressure may be selectable between a predetermined range. Then based on the size of the compression paddle and the compression pressure required or desired, the image system calculates a target force, operation 1106.

Once the target force is calculated, a compressive force may be applied to the breast as described herein. In an example, the calculated target force may be used for adjusting torque resistance on the knob as described above in reference to FIG. 8.

EXAMPLES

Illustrative examples of the systems and methods described herein are provided below. An embodiment of the system or method described herein may include any one or more, and any combination of, the clauses described below.

Clause 1. A method of compressing a breast of a patient with a breast imaging system, the method including:
obtaining an x-ray area of the breast of the patient, wherein the x-ray area is obtained from a prior x-ray image of the breast of the patient;
comparing the x-ray area of the breast to a data set;
based at least in part on the comparison, identifying a target force, wherein the data set relates the x-ray area of the breast to the target force;
applying a compressive force to the breast, wherein the compressive force is based at least in part on the target force; and
imaging the breast with the breast imaging system.

Clause 2. The method of any one of clauses 1-10, wherein when the prior x-ray image of the breast is unavailable, obtaining the x-ray area includes:
receiving a distance measurement of a distance of a nipple of the breast from a chest wall of the patient; and
estimating the x-ray area based at least in part on the received distance measurement.

Clause 3. The method of any one of clauses 1-10, wherein estimating the x-ray area includes comparing the distance measurement to a reference distance obtained from a reference.

Clause 4. The method of any one of clauses 1-10, wherein the target force is obtained from a look-up table.

Clause 5. The method of any one of clauses 1-10, wherein the target force is obtained by applying the x-ray area to an algorithm.

Clause 6. The method of any one of clauses 1-10, further including, prior to imaging the breast, emitting a threshold signal when the applied force is within a first predetermined threshold of the target force.

Clause 7. The method of any one of clauses 1-10, further including, prior to imaging the breast, emitting a target signal when the applied force is within a second predetermined threshold of the target force.

Clause 8. The method of any one of clauses 1-10, wherein at least one of the threshold signal and the target signal includes at least one of a visual signal and an audible signal.

Clause 9. The method of any one of clauses 1-10, wherein at least one of the threshold signal and the target signal includes a control signal for controlling a compression arm of the breast imaging system.

Clause 10. The method of any one of clauses 1-10, further including, applying tactile feedback during manual compression based at least in part on the target force.

Clause 11. A method of guiding compression of a breast of a patient with a breast imaging system, the method including:
obtaining an x-ray area of the breast of the patient;
calculating a target force based at least in part on the x-ray area; and
based at least in part on the calculation, sending a target force signal to a compression arm of the breast imaging system.

Clause 12. The method of any one of clauses 11-18, wherein the x-ray area is obtained from a storage device.

Clause 13. The method of any one of clauses 11-18, wherein the storage device is remote from the breast imaging system.

Clause 14. The method of any one of clauses 11-18, wherein the storage device includes at least one prior image of the breast of the patient and at least one prior image of another patient.

Clause 15. The method of any one of clauses 11-18, wherein the x-ray area is obtained from a prior x-ray image of the breast of the patient.

Clause 16. The method of any one of clauses 12-19, wherein when the prior x-ray image of the breast is unavailable, obtaining the x-ray area includes:
receiving a distance measurement of a distance of a nipple of the breast from a chest wall of the patient; and
estimating the x-ray area based at least in part on the received distance measurement.

Clause 17. The method of any one of clauses 11-18, wherein estimating the x-ray area includes comparing the distance measurement to a reference distance obtained from a reference.

Clause 18. The method of any one of clauses 11-18, wherein obtaining the x-ray area is based on a size of a compression paddle.

Clause 19. A breast imaging system including:
an x-ray source;

a breast support platform;
an x-ray detector disposed below the breast support platform;
a compression arm disposed between the x-ray source and the breast support platform;
a processor;
a signal emitter connected to the processor; and
memory storing instructions that when executed by the processor cause the breast imaging system to perform a set of operations including:
  obtaining an x-ray area of the breast of the patient, wherein the x-ray area is obtained from a prior x-ray image of the breast of the patient;
  comparing the x-ray area of the breast to a data set;
  based at least in part on the comparison, identifying a target force, wherein the data set relates the x-ray area of the breast to the target force;
  applying a compressive force to the breast with the compression arm, wherein the compressive force is based at least in part on the target force; and
  imaging the breast by emitting an x-ray energy from the x-ray source and receiving the x-ray energy at the x-ray detector.

Clause 20. The system of any one of clauses 19-25, wherein the set of operations further includes, prior to imaging the breast, emitting a threshold signal from the signal emitter when the applied compressive force is within a first predetermined threshold of the target force.

Clause 21. The system of any one of clauses 19-25, wherein the set of operations further includes, prior to imaging the breast, emitting a target signal from the signal emitter when the applied compressive force is within a second predetermined threshold of the target force.

Clause 22. The system of any one of clauses 19-25, wherein the signal emitter is at least one of an audio emitter and a visual emitter.

Clause 23. The system of any one of clauses 19-25, wherein the signal emitter includes a display.

Clause 24. The system of any one of clauses 19-25, wherein the x-ray area of the breast is based at least in part on a breast thickness.

Clause 25. The system of any one of clauses 19-25, wherein the set of operation further includes, applying tactile feedback during manual compression based at least in part on the target force.

Clause 26. A method of compressing a breast of a patient with a breast imaging system, the method including:
determining a compression surface area of a compression paddle;
determining compression pressure for the breast;
calculating a target force based at least in part on the determined compression surface area and the compression pressure;
applying a compressive force to the breast, wherein the compressive force is based at least in part on the target force; and
imaging the breast with the breast imaging system.

Clause 27. The method of any one of clauses 26-33, wherein determining the compression surface area of the compression paddle further includes reducing the compression surface area by a predetermined value.

Clause 28. The method of any one of clauses 26-33, wherein determining the compression surface area of the compression paddle is performed by the detection of the compression paddle on the breast imaging system.

Clause 29. The method of any one of clauses 26-33, further including, prior to imaging the breast, emitting a threshold signal when the applied force is within a first predetermined threshold of the target force.

Clause 30. The method of any one of clauses 26-33, further including, prior to imaging the breast, emitting a target signal when the applied force is within a second predetermined threshold of the target force.

Clause 31. The method of any one of clauses 26-33, wherein at least one of the threshold signal and the target signal includes at least one of a visual signal and an audible signal.

Clause 32. The method of any one of clauses 26-33, wherein at least one of the threshold signal and the target signal includes a control signal for controlling a compression arm of the breast imaging system.

Clause 33. The method of any one of clauses 26-33, further including, applying tactile feedback during manual compression based at least in part on the target force.

Clause 34. A method of guiding compression of a breast of a patient with a breast imaging system, the method including:
obtaining an x-ray area of the breast of the patient;
calculating a target force based at least in part on the x-ray area; and
based at least in part on the calculation, adjusting torque resistance on a knob of a compression arm of the breast imaging system.

Clause 35. The method of any one of clauses 33-41, wherein the x-ray area is obtained from a storage device.

Clause 36. The method of any one of clauses 33-41, wherein the storage device is remote from the breast imaging system.

Clause 37. The method of any one of clauses 33-41, wherein the storage device includes at least one prior image of the breast of the patient and at least one prior image of another patient.

Clause 38. The method of any one of clauses 33-41, wherein the x-ray area is obtained from a prior x-ray image of the breast of the patient.

Clause 39. The method of any one of clauses 33-41, wherein when the prior x-ray image of the breast is unavailable, obtaining the x-ray area includes:
receiving a distance measurement of a distance of a nipple of the breast from a chest wall of the patient; and
estimating the x-ray area based at least in part on the received distance measurement.

Clause 40. The method of any one of clauses 33-41, wherein estimating the x-ray area includes comparing the distance measurement to a reference distance obtained from a reference.

Clause 41. The method of any one of clauses 33-41, wherein obtaining the x-ray area is based on a size of a compression paddle.

Clause 42. A breast imaging system including:
an x-ray source;
a breast support platform;
an x-ray detector disposed below the breast support platform;
a compression arm disposed between the x-ray source and the breast support platform;

a processor;
a signal emitter connected to the processor; and
memory storing instructions that when executed by the processor cause the breast imaging system to perform a set of operations including:
  determining a compression surface area of a compression paddle;
  determining compression pressure for the breast;
  calculating a target force based at least in part on the determined compression surface area and the compression pressure;
  applying a compressive force to the breast, wherein the compressive force is based at least in part on the target force; and
  imaging the breast by emitting an x-ray energy from the x-ray source and receiving the x-ray energy at the x-ray detector.

Clause 43. The system of any one of clauses 42-47, wherein the set of operations further includes, prior to imaging the breast, emitting a threshold signal from the signal emitter when the applied compressive force is within a first predetermined threshold of the target force.

Clause 44. The system of any one of clauses 42-47, wherein the set of operations further includes, prior to imaging the breast, emitting a target signal from the signal emitter when the applied compressive force is within a second predetermined threshold of the target force.

Clause 45. The system of any one of clauses 42-47, wherein the signal emitter is at least one of an audio emitter and a visual emitter.

Clause 46. The system of any one of clauses 42-47, wherein the signal emitter includes a display.

Clause 47. The system of any one of clauses 42-47, wherein the set of operation further includes, applying tactile feedback during manual compression based at least in part on the target force.

This disclosure described some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

What is claimed is:

1. A method of compressing a breast of a patient with a breast imaging system, the method comprising:
  obtaining a prior x-ray image of the breast of the patient;
  determining an x-ray image area of the breast of the patient from the prior x-ray as a numerical value;
  comparing the x-ray image area of the breast to a data set;
  based at least in part on the comparison, identifying a target force, wherein the data set relates the x-ray image area of the breast to the target force;
  applying a compressive force to the breast, wherein the compressive force is based at least in part on the target force; and
  imaging the breast with the breast imaging system.

2. The method of claim 1, wherein when the prior x-ray image of the breast is unavailable, obtaining the x-ray image area comprises:
  receiving a distance measurement of a distance of a nipple of the breast from a chest wall of the patient; and
  estimating the x-ray image area based at least in part on the received distance measurement.

3. The method of claim 2, wherein estimating the x-ray image area comprises comparing the distance measurement to a reference distance obtained from a reference.

4. The method of claim 1, wherein the target force is obtained from a look-up table or obtained by applying the x-ray image area to an algorithm.

5. The method of claim 1, further comprising, prior to imaging the breast, emitting a threshold signal when the applied force is within a first predetermined threshold of the target force.

6. The method of claim 5, further comprising, prior to imaging the breast, emitting a target signal when the applied force is within a second predetermined threshold of the target force.

7. The method of claim 6, wherein at least one of the threshold signal and the target signal comprises at least one of a visual signal and an audible signal.

8. The method of claim 6, wherein at least one of the threshold signal and the target signal comprises a control signal for controlling a compression arm of the breast imaging system.

9. The method of claim 1, further comprising, applying tactile feedback during manual compression based at least in part on the target force.

10. A method of guiding compression of a breast of a patient with a breast imaging system, the method comprising:
  obtaining a prior x-ray image of the breast of the patient;
  determining an x-ray image area of the breast of the patient from the prior x-ray as a numerical value;
  calculating a target force based at least in part on the x-ray image area; and
  based at least in part on the calculation, sending a target force signal to a compression arm of the breast imaging system.

11. The method of claim 10, wherein the x-ray image area is obtained from a storage device that is remote from the breast imaging system.

12. The method of claim 11, wherein the storage device comprises at least one prior image of the breast of the patient and at least one prior image of another patient.

13. The method of claim 10, wherein the x-ray image area is obtained from a prior x-ray image of the breast of the patient.

14. The method of claim 13, wherein when the prior x-ray image of the breast is unavailable, obtaining the x-ray image area comprises:
  receiving a distance measurement of a distance of a nipple of the breast from a chest wall of the patient; and
  estimating the x-ray image area based at least in part on the received distance measurement, wherein estimating the x-ray image area comprises comparing the distance measurement to a reference distance obtained from a reference.

15. The method of claim 10, wherein obtaining the x-ray image area is based on a size of a compression paddle.

16. A breast imaging system comprising:
an x-ray source;
a breast support platform;
an x-ray detector disposed below the breast support platform;
a compression arm disposed between the x-ray source and the breast support platform;
a processor;
a signal emitter connected to the processor; and
memory storing instructions that when executed by the processor cause the breast imaging system to perform a set of operations comprising:
   obtaining a prior x-ray image of the breast of the patient;
   determining an x-ray image area of the breast of the patient from the prior x-ray as a numerical value;
   comparing the x-ray image area of the breast to a data set;
   based at least in part on the comparison, identifying a target force, wherein the data set relates the x-ray image area of the breast to the target force;
   applying a compressive force to the breast with the compression arm, wherein the compressive force is based at least in part on the target force; and
   imaging the breast by emitting an x-ray energy from the x-ray source and receiving the x-ray energy at the x-ray detector.

17. The system of claim 16, wherein the set of operations further comprises, prior to imaging the breast, emitting a threshold signal from the signal emitter when the applied compressive force is within a first predetermined threshold of the target force.

18. The system of claim 17, wherein the set of operations further comprises, prior to imaging the breast, emitting a target signal from the signal emitter when the applied compressive force is within a second predetermined threshold of the target force.

19. The system of claim 18, wherein the signal emitter is at least one of an audio emitter and a visual emitter.

20. The system of claim 16, wherein the signal emitter comprises a display.

21. The system of claim 16, wherein the x-ray image area of the breast is based at least in part on a breast thickness.

22. The system of claim 16, wherein the set of operation further comprises, applying tactile feedback during manual compression based at least in part on the target force.

23. The method of claim 1, wherein determining the x-ray image area comprises counting a number of pixels representing the breast in the prior x-ray image.

24. The method of claim 1, wherein applying the compressive force comprises applying one of a median compressive force and an average compressive force from compressive forces that are applied to breasts for a population sharing one or more similarities with the patient, the one or more similarities including at least one of geographic location, age, and breast density.

25. The method of claim 1, wherein applying the compressive force comprises:
   generating a relationship between x-ray image areas and compressive forces for a population sharing one or more similarities with the patient;
   calculating a target compressive force based on the determined x-ray image area of the breast of the patient and the generated relationship; and
   applying the compressive force to correspond to the target compressive force.

* * * * *